United States Patent [19]

Miller et al.

[11] Patent Number: 5,417,100

[45] Date of Patent: May 23, 1995

[54] REVERSIBLE SENSOR FOR DETECTING SOLVENT VAPORS

[75] Inventors: Leroy J. Miller, West Hills; Camille I. van Ast; Frederick G. Yamagishi, both of Newbury Park, all of Calif.

[73] Assignee: Hughes Aircraft Company, Los Angeles, Calif.

[21] Appl. No.: 29,805

[22] Filed: Mar. 10, 1993

[51] Int. Cl.6 .................... G01N 27/00; G01R 27/22
[52] U.S. Cl. ......................... 73/31.02; 73/31.01; 73/31.03; 204/424; 324/439; 324/446; 324/691; 324/693; 428/426; 428/458; 428/421
[58] Field of Search ............... 73/29.05, 31.01, 31.02, 73/31.03; 428/421, 913, 426, 461, 458, 446; 324/439, 446, 693, 722, 724, 691; 204/424, 427, 412

[56] References Cited

U.S. PATENT DOCUMENTS

| | | | |
|---|---|---|---|
| 4,631,952 | 12/1986 | Donaghey | 73/23 |
| 4,812,221 | 3/1989 | Madou et al. | 204/412 |
| 5,023,133 | 6/1991 | Yodice et al. | 428/332 |
| 5,089,780 | 2/1992 | Megerle | 324/448 |
| 5,137,991 | 8/1992 | Epstein et al. | 525/540 |

FOREIGN PATENT DOCUMENTS

0442314A2  8/1991  European Pat. Off. .

OTHER PUBLICATIONS

J. Phys. Chem. 1985, 89, 1441-1447, "Resistance of Polyaniline Films as a Function of Electrochemical Potential and the Fabrication of Polyaniline-Based Microelectronic Devices", E. Paul, et al.

Synthetic Metals, 13, 1986, 193-205, 'Polyaniline': Protonic Acid Doping of the Emeraldine Form to the Metallic Regime, J. Chiang et al.

P. N. Bartlett et al, "Conducting Polymer Gas Sensors", in Sensors and Actuators, vol. 20, pp. 287-292 (1989).

*Primary Examiner*—Paul J. Thibodeau
*Assistant Examiner*—Stephen Sand
*Attorney, Agent, or Firm*—V. D. Duraiswamy; W. K. Denson-Low

[57] ABSTRACT

A novel, inexpensive sensor (10) for detecting volatile hydrocarbons and other solvent vapors detects leaks in the fittings and valves of petroleum refineries and chemical manufacturing and processing plants. The sensor comprises (a) a dielectric substrate (12) having a major surface; (b) a pair of interdigitated, electrically conductive electrodes (14a, 14b) disposed on the major surface of the substrate; and (c) a composite coating (16) covering the interdigitated electrodes and comprising (1) a conductive polymer, and (2) a dielectric polymer with an affinity for the solvent vapors to be detected.

15 Claims, 5 Drawing Sheets

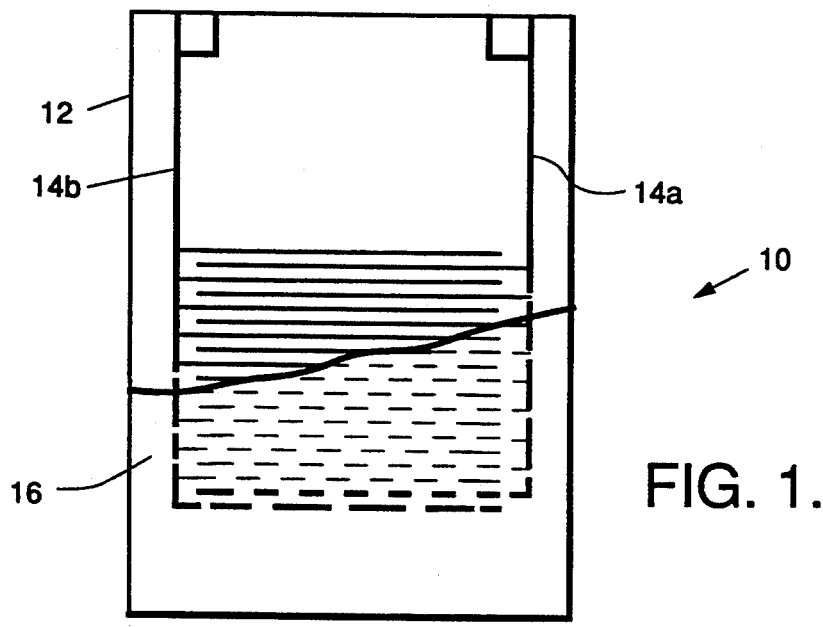
FIG. 1.
FIG. 2
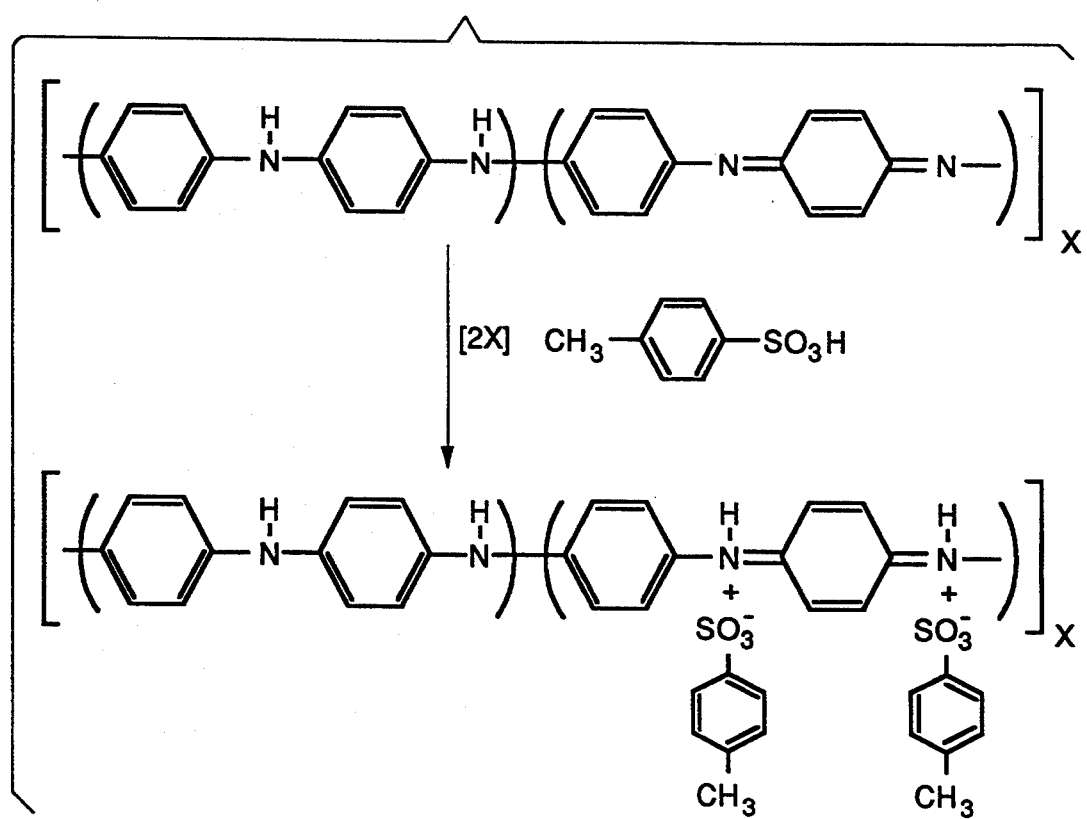

REVERSIBLE SENSOR FOR DETECTING SOLVENT VAPORS

BACKGROUND OF THE INVENTION

1. Field of the Invention

The present invention relates to sensors for sensing gases, and, more particularly, to sensors for sensing gaseous leaks from valves, flanges, fittings, and the like, in chemical and petroleum plant (or refinery) environments.

2. Description of Related Art

Gaseous emissions are of two types: (a) stack gas emissions, and (b) fugitive emissions (i.e., leaks), which are about half of the total emissions. Major chemical companies say they will reduce their emissions by about 90% over the next 5 years. It will be impossible for them to comply without reducing fugitive emissions.

Most of the industrial air pollutant emissions are generated by two types of companies, chemical manufacturing companies and oil refineries, in which there is a huge potential for fugitive emissions. Both types of companies have processing facilities that are characterized by a large number of valves, flanges, and fittings, each of which is a potential source of fugitive emissions. A typical facility will have about 40,000 valves and about four to six times as many flanges, or about 100,000 to 300,000 of these potential leak sources.

Currently, personnel with sniffers walk through the facility periodically and check for leaks. If there is a continuous problem with a valve or fitting, it is bagged and samples are taken for analysis by gas chromatography. High leakers, defined as those with 50,000 ppm or more of hydrocarbons in the surrounding atmosphere, must be identified quickly and repaired within 24 hours. A leaker is defined as a fitting with 500 ppm or more hydrocarbon in the surrounding air, although some companies use a lower value.

The hand-held sniffer typically contains a flame ionization detector. Some fittings are checked as infrequently as once or twice a year. If a fitting leaks, the leak will continue until the next check period. These leaks also present an explosion hazard if they go undetected.

The usual sniffer consists of a long tube through which air samples are sucked to reach the flame ionization detector. There is often difficulty in reaching some valves, such as those near the ceiling, or those on a offshore rig, for sampling. The current maintenance program is costing the petroleum industry about $1 to $4 per year per component for leak detection.

There is also a big problem with data management. Each fitting must be recorded when it is checked. Systems with leaking valves must also be taken off line to make replacements, and one must be sure that the correct valve is being replaced, because all this is very costly.

A critical, large, and currently unmet need is the ability to place inexpensive monitors at a significant number of these sites, and to do this easily and flexibly. Readings from these sensors would be monitored and recorded by a computer, which would also notify the operators immediately when and where a leak has occurred. The detection of leaks on a daily basis would enable the operators to fix the leaks in a more timely fashion, so that the overall quantity of fugitive emissions would be greatly reduced.

The specificity of the sensor can be very low, since the operators of the plant know what is in the system. Sources of ignition, such as flames, hot wires, or hot catalytic surfaces, which are present in the sensors that are currently available, must be avoided because of explosion hazards. The sensitivity of the sensors can be quite low, since they can be placed near the source of the leak, or the leak can be partially confined in the region of the sensor, and the sensor can be placed in the confined region where the vapor concentration is very high. A sensor chip would be ideal.

SUMMARY OF THE INVENTION

In accordance with the invention, a sensor is provided for detecting fugitive emissions. The sensor comprises:

(a) a dielectric substrate having a major surface;

(b) a pair of interdigitated, electrically conductive electrodes on the major surface of the substrate, comprising a material that is unreactive with the other components of the sensor or with the vapors present in the surrounding atmosphere; and (c) a composite coating covering the interdigitated electrodes and comprising (1) a conductive polymer, and (2) a dielectric polymer with an affinity for the solvent vapors to be detected.

The sensor of the present invention can detect a leak as small as 10 $\mu$L of a typical hydrocarbon, hexane. This corresponds to 0.0065 g.

The cost of these sensors is low. It is estimated that the sensors could be manufactured for significantly less than $1.

The power requirements are very low (e.g., about 1 to 10 mW per sensor). The sensor operates at ambient temperature, so there is no danger of causing an explosion.

BRIEF DESCRIPTION OF THE DRAWINGS

FIG. 1 is a top plan view of the fugitive emissions sensor of the invention;

FIG. 2 depicts the chemical structure of the insulating emeraldine base form and the conductive emeraldine salt form of polyaniline, shown as the p-toluenesulfonate salt, which is employed as a conducting polymer in the practice of the invention;

DESCRIPTION OF THE PREFERRED EMBODIMENTS

Figure 3:
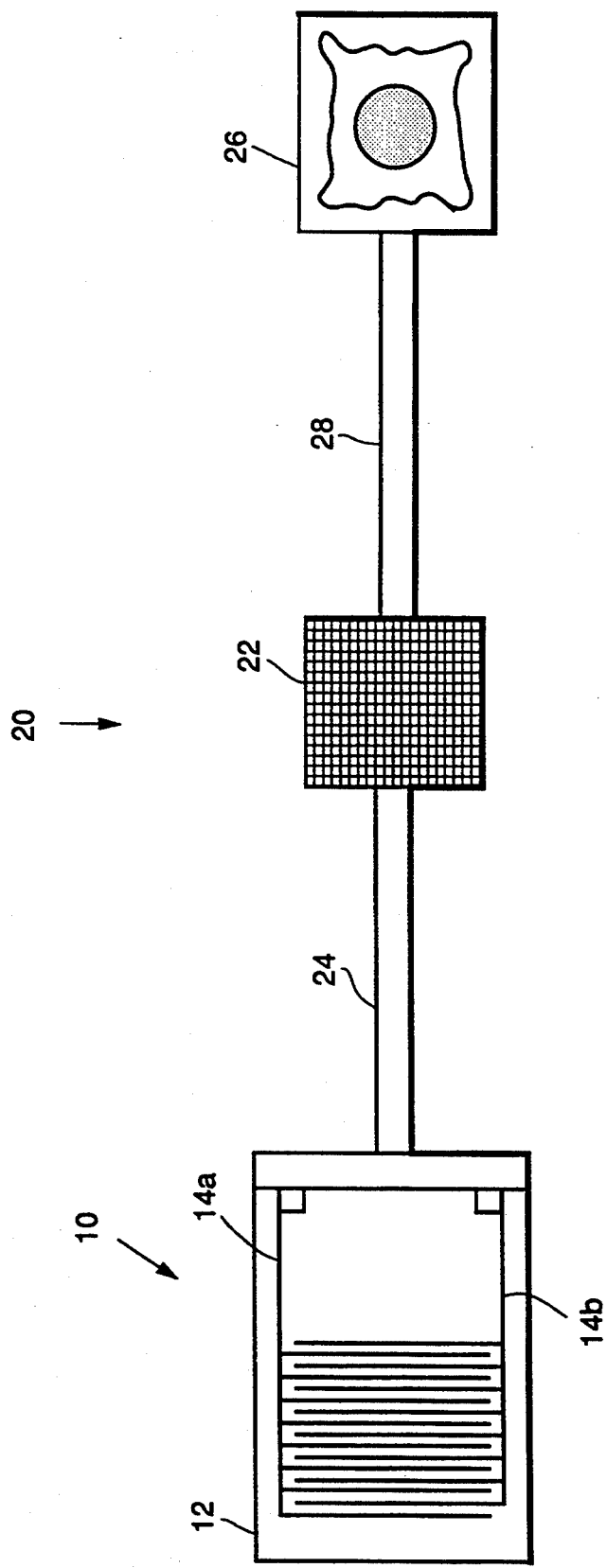
FIG. 3 is a schematic diagram showing implementation of the sensor of the invention in an alarm system.

FIG. 1 depicts the sensor 10 of the invention. This sensor is capable of detecting volatile hydrocarbons and other organic solvent vapors. The sensor 10 comprises (1) a dielectric substrate 12; (2) a pair of interdigitated, electrically conductive electrodes 14a, 14b disposed on the surface of the substrate; and (3) a composite coating 16 comprising (a) a conductive polymer; and (b) a dielectric polymer with an affinity for the solvent vapors that one wishes to detect.

Examples of suitable dielectric substrates 12 include glass and ceramics. In this connection, any of the common silica-based, phosphate-based, borate-based or other oxide-based glasses or mixtures of these may be employed in the practice of the invention. Further, any of the common oxide ceramics, such as alumina, magnesia, calcia, quartz, and the like and mixtures of these may be employed in the practice of the invention. Alternatively, any dielectric polymer having a low affinity for hydrocarbon vapors may be employed in the practice of the invention. Examples of such dielectric polymers include polyethylene terephthalate, fluorinated polymers (such as Teflon), the acrylics, such as polymethyl methacrylate, and polyimides, such as Kapton.

The electrically conductive electrodes 14a, 14b generally comprise a conductive metal or metals, and preferably comprise metals that have no reactivity with the other components of the sensor or with the vapors present in the surrounding atmosphere. An example of a metal that has been used for the pair of interdigitated electrodes 14a, 14b is gold, which was formed over a tungsten-titanium alloy, the alloy serving to provide good adhesion of the gold to the glass substrate 12. Other suitable conductive materials include platinum, palladium, and carbon. As with gold, an adhesion layer, employing any of the well-known adhesion layer materials, may be employed in conjunction with the metal electrodes 14a, 14b. The thickness of such adhesion layers is on the order of tens of Ångstroms.

The interdigitated electrodes are formed by conventional photolithographic techniques, and such process does not form a part of this invention. Typically, the metal layer is blanket-deposited and patterned.

The parameters of the interdigitation (number of finger pairs, length of fingers, width of fingers, periodicity, and electrode thickness) are not critical. For exemplary purposes only, gold interdigitation may comprise 50 finger pairs, with each finger about 5 mm long, 25 $\mu$m wide, with a 60 $\mu$m period, and about 2 $\mu$m thick.

The conductive polymer in the composite coating 16 is one having a conductivity of about $10^{-6}$ to 1 S/cm. However, it is not the conductivity that is as important in the practice of the invention as is the change in conductivity as the sensor experiences different environments. Such change in conductivity is measured by a change in current, and can range as small as about 5 $\mu$A to several mA.

Examples of conductive polymers suitably employed in the practice of the invention include polyaniline, polythiophene, polypyrrole, poly(p-phenylene vinylene), derivatives of these polymers, or mixtures of these materials. The conductive polymers are doped with appropriate dopants for these materials to provide them with the requisite conductivity, as indicated above.

The polymer must also be in the appropriate oxidation state to exhibit conductivity. For polymers such as polythiophene and polypyrrole, which require specific dopants, the presence of the dopant provides the appropriate oxidation state, changing the polymer from a neutral state to a charged state. For polymers such as polyaniline, which only require protonation to be rendered conductive, it is desired that the polymer be in a state that is intermediate to the fully oxidized state and the fully reduced state. In the case of polyaniline, such an intermediate state is referred to as the emeraldine state.

As an example, polyaniline is prepared in the emeraldine oxidation state as an appropriate salt, as illustrated in FIG. 2. The acid used to make this salt can be considered to be a dopant for the polymer, due to protonation. Salts of sulfonic acids, such as p-toluenesulfonic acid, benzenesulfonic acid, p-dodecylsulfonic acid, or poly(styrenesulfonic acid), or mineral acids, such as sulfuric acid, hydrochloric acid, and the like can be used; however, p-toluenesulfonic acid is a preferred acid for this application.

Examples of derivatives of the conductive polymers employed in the practice of the invention are those with substituents on the aromatic rings. These substituents include alkyl and alkoxy groups.

The amount of dopant to provide the requisite conductivity is about 0.5 mole per mole of polymer.

The dielectric polymers in the composite layer 16 are selected to be strongly swelled by the solvent whose vapors are to be detected. For an application in which it is desired to detect hydrocarbon vapors, polymers are selected that are swelled by hydrocarbon solvents. Such polymers include poly(isobutylene), polybutadiene, polystyrene, and alkyl-substituted polystyrenes. Other vapors that may be detected by the sensor of the invention are polar solvents, such as alcohols, ketones, and even water. Polymers for detecting such polar solvents could include polyvinyl alcohol (for detecting alcohols) and other polymers containing polar groups (e.g., amino, hydroxyl, carboxylate), such as some nylons and some polymeric salts such as Surlyn, which is a poly(sodium acrylate).

The thickness of the composite coating must be sufficient to cover the gap between the interdigits, but not so thick as to crack. Coatings on the order of 25 $\mu$m are considered to be appropriate, although the thickness may vary, depending on the size of the gap.

It appears that the sensor of the invention relies on physical absorption of the vapor being detected. The absorbed vapor causes a change in the polymer morphology, such as by swelling, which changes the distance from one conductive polymer chain to the next, thereby altering the conductivity. In the case of a polar solvent vapor, there is an additional mechanism, caused by the presence of polar groups in the absorbed species, which further alters the conductivity of the conductive polymer. In either event, removing the sensor from the presence of the vapor being detected and placing it in ambient air allows the absorbed species to desorb and results in return of the sensor to its original conductivity. Thus, the sensor of the invention may be cycled repeatedly in detecting a given species.

In general terms, while a sensor may detect a given species in a matter of seconds or minutes, the amount of time required for the sensor to recover its original conductivity by exposure to ambient air is measured in terms of hours or days. Thus, the time required for the sensor to recover original conductivity dominates the sensor's total cycle time. However, the sensor of the invention evidences partial recovery of its original conductivity as quickly as one minute after being placed in ambient air. Examples 1 and 2 illustrate these time-related features of the invention.

The ratio of the conductive polymer to the dielectric polymer is governed by the fact that a higher concentration of conductive polymer results in a sensor having higher conductivity, but lower sensitivity, whereas reducing the concentration of the conductive polymer increases the sensitivity of the sensor, but lowers the conductivity. Consistent with these considerations, a ratio of about 1:1 to 1:5 is desirably employed. In the case of polyaniline (conductive polymer, PA) and polyisobutylene (dielectric polymer, PIB) for detecting hydrocarbons, a ratio of about 1:4 of PA:PIB was found to be optimum.

The sensor of the present invention can detect a leak as small as 10 μL of a typical hydrocarbon, hexane. This corresponds to 0.0065 g. The EPA estimates that typical fugitive emissions from leaking valves is 5.6 g/hr and from leaking flanges is 0.83 g/hr. A leak of 100 μL (about 0.065 g) or more per hour could easily be programmed to set off an alarm to notify the operator. To do this, the sensor could be confined inside a plastic (e.g., Mylar) wrapping around the potential leak source. A small opening would be provided to keep the internal and external pressures equal. The sensitivity will depend on the internal volume of the wrapped space, and on the size of the opening to the external environment.

The cost of these sensors would be very low. Improvements in design may also be envisioned that would allow the electrodes and the sensor composite polymer film to be "printed" on a plastic backing. The sensor could be stapled to the wrapping, and the staples could also be the leads to the electrodes. In this way, the cost of the sensor itself could probably be brought down to less than $1.

The power requirements are very low (e.g., about 1 to 10 mW per sensor). The sensor operates at ambient temperature, so there is no danger of causing an explosion.

A leak in a valve or flange will cause a change in conductivity in the sensor of the invention. The signal caused by the change in conductivity can be monitored through wiring to an ammeter and subsequently read by a computer. Alternatively, the electrical signals from the sensor can be converted to optical pulses which can be detected by an appropriate detector (e.g., photodiode) or transmitted through fiber optic lines, then converted to electrical signals at the ammeter. The computer may be programmed with an algorithm to detect threshold current values that would define a leak, along with time constants, and other pertinent variables, such as temperature. Correlation of these parameters will determine a point when an "alarm" should be turned on. The alarm could be in the form of an audible tone (e.g., bell, siren, etc.), a flashing light, or combination thereof. FIG. 3 depicts an example of an alarm system 20 comprising the sensor 10 of the invention, linked to a computer 22 which includes an ammeter, through signal transmission means 24. The computer 22 in turn is linked to an alarm 26 by signal transmission means 28.

The following examples are provided to illustrate the preparation and properties of the sensor of the invention.

EXAMPLES

Example 1

A 10% solution (w/v) of poly(iso-butylene) (Polysciences, average molecular weight of 10,800) was prepared in heptane. Polyaniline doped with p-toluenesulfonic acid (M1702-18, synthesized as described further below) (0.1 g) was added to 2 mL of this solution and the mixture was stirred rapidly with a homogenizer until the solid polyaniline particles were very small. A drop of this slurry was placed over gold interdigitated electrodes on a glass slide. The electrodes consisted of 50 finger or digit pairs, each 5 mm long and 25 μm wide, with a 60 μm period, 2 μm thick. The gold electrodes were sputter-deposited over a thin layer of sputter-deposited tungsten-titanium alloy, about 25 to 100 Å thick, employing photolithography to define the interdigitated electrodes. The solvent of the slurry was allowed to evaporate in air over a period of several hours, followed by complete evaporation under vacuum, to produce a composite film coating of poly(isobutylene) and polyaniline.

A dc voltage of 0.2 V was applied between the electrodes, and the current was 2.5 mA. The sensor was placed in an aqueous solution containing sulfuric acid (0.6M), sodium hydrogen sulfate (0.5M), and aniline (0.44M, in solution as the anilinium salt). The two interdigitated electrodes were connected and made the anode, while a platinum mesh was made the cathode, and polyaniline was deposited over the composite film by cyclic voltammetry. The potential was cycled between 0 and 900 mV dc at a rate of 50 mV/sec with reference to a saturated calomel electrode, and polyaniline was deposited during four cycles. The sensor was rinsed in water. The device was then placed in an aqueous acid solution containing only sulfuric acid (0.6M) and sodium hydrogen sulfate (0.5M) and the polyaniline coating was cycled again between 0 and 900 mV dc at a rate of 50 mV/sec using the same conditions as above. This time the voltage was cycled from 0 to 900 mV, back to 0 mV, and then to 400 mV. The sensor was rinsed in water and dried in air.

The current between the two interdigitated electrodes was measured with an applied voltage of 0.2 V dc, and the current was 38.9 mA in ambient laboratory air. The sensor was tested by placing it over a container of hexane. The current dropped to 26.2 mA. The sensor was then allowed to recover for one minute in air, and the current rose to 27.8 mA. Next, the sensor was placed over a container of toluene, and in 1 minute the current dropped to 25.1 mA. Again the sensor was allowed to partially recover in air for 2 minutes, during which the current rose to 26.8 mA. Then, the sensor was placed over a container of methanol, and after 2 minutes, the current rose to 28.3 mA. When the sensor was allowed to recover in laboratory air for 20 minutes, the current rose to 31.2 mA. The sensor was placed over hexane again, and after 1 minute the current dropped to 13.4 mA.

The polyaniline M1702-18 used in the preparation of the sensor above was synthesized as follows:

Aniline (Aldrich, 99+%, 25.55 g) was added to a stirred solution of p-toluenesulfonic acid monohydrate (190.22 g) in 700 mL of deionized water and then cooled to ≃10° C. Ammonium persulfate (228.19 g) dissolved in 350 mL of water was added dropwise over a period of 50 min. When the addition was completed, the mixture was allowed to come to room temperature with continued stirring. After 19 hrs, the green-black solid which had formed was filtered off and washed five times with 70 mL portions of water. This material was dried at 50° C. under vacuum to yield 38.53 g of polyaniline M1702-18. It was crushed and stored in a bottle. The material was about 4 years old when it was used to prepare the sensors.

Example 2

Four new slurries of polyaniline (M1702-18) in a 10% (w/v) solution of poly(iso-butylene) in heptane were prepared using a sonicator to mix them and to reduce the size of the solid polyaniline particles. These slurries had weight ratios of polyaniline to poly(iso-butylene) of 1:1, 1:2, 1:3, and 1:4. Sensors were prepared with interdigitated electrodes on glass as described in Example 1. In this example, each sensor was prepared simply by placing a drop of a slurry over the electrodes and allowing it to dry in air and then in vacuum at room temperature for a period of 4 to 16 hr.

Sensor 130a was prepared with a ratio of 1:1. The current between the two interdigitated electrodes was measured with an applied voltage of 0.2 V dc, and the current was 31.3 mA in ambient laboratory air. The sensor was tested by placing it over a container of hexane. The current dropped to 29.46 mA in 20 sec. The sensor was then allowed to recover for 3 min in air, and the current rose to 30.8 mA.

Sensor 130B1 was prepared with a ratio of 1:2. The current between the two interdigitated electrodes was measured with an applied voltage of 0.2 V dc, and the current was 35.5 mA in ambient laboratory air. The sensor was tested by placing it over a container of hexane. The current dropped to 13.0 mA in 6 min. The sensor was then allowed to recover for 60 hr in air, and the current rose to 35.8 mA. The sensor was then place over an open container of toluene, and within 6 min the current dropped to 18.2 mA. After 2 hr in laboratory air the current returned to 31.6 mA.

Figure 4:
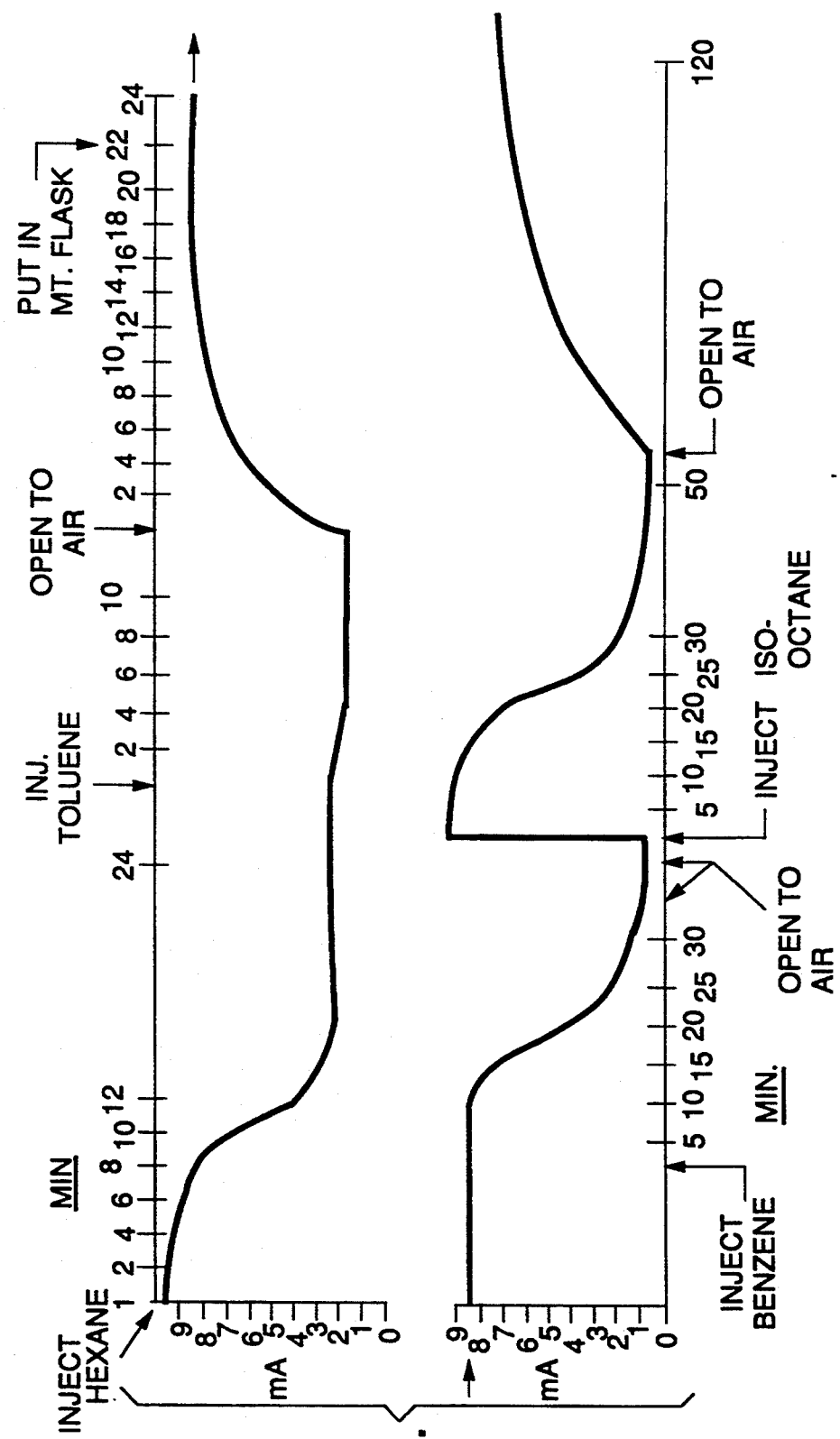
FIG. 4, on coordinates of current (in mA) and time (in minutes), is a plot of current as a function of time employing one embodiment of the device of the invention in response to hexane.

Sensor 140-5 was prepared with a ratio of 1:3. The current between the two interdigitated electrodes was measured with an applied voltage of 0.2 V dc, and the current was 9.3 mA in ambient laboratory air. The sensor was then tested in a 100-mL flask closed with rubber septa except for a hollow needle inserted through a septum to serve as a vent to air. A syringe was used to inject samples of solvents, and the current was measured as a function of time. The results are given in FIG. 4, which also shows the current during those periods when the sensor was removed from the flask into ambient laboratory air. As FIG. 4 shows, the current dropped to 2.1 mA after 100 μL of hexane was injected, and it dropped further to 1.3 mA when 100 μL of toluene was injected. After allowing the sensor to recover in laboratory air, it was again placed in a clean, dry flask, and 100 μL of benzene was injected. As further shown in FIG. 4, this caused the current to drop from 8.3 mA to 1.3 mA. After allowing the vapors to desorb from the sensor overnight in laboratory air, the current was 9.0 mA. The sensor was once more placed in a clean flask, and 100 μL of iso-octane was injected. The current dropped to 0.59 mA as a result of exposure to the iso-octane vapors.

Figure 5:
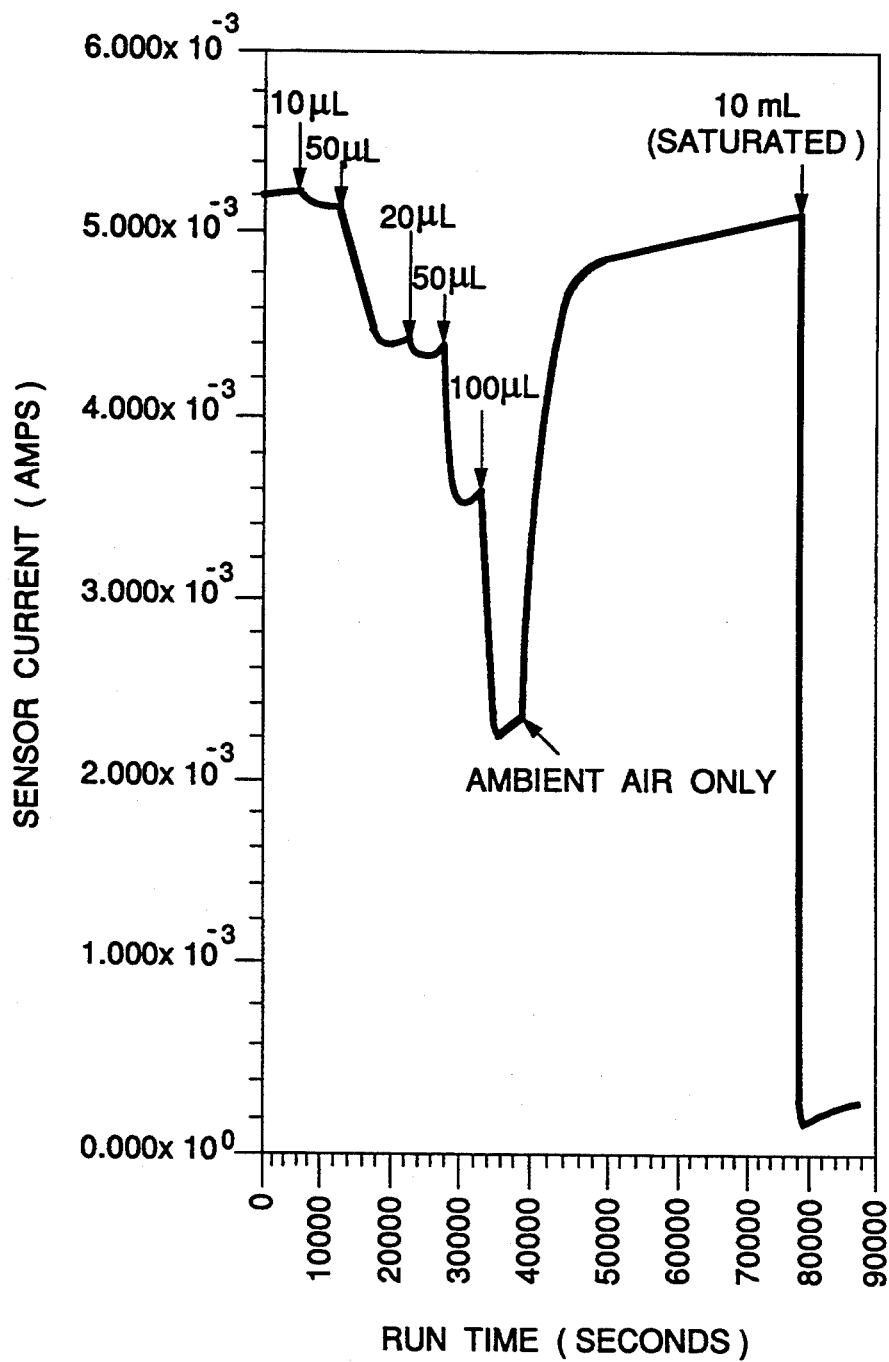
FIG. 5, on coordinates of sensor current (in A) and time (in seconds), is a plot of current as a function of time employing another embodiment of the device of the invention in response to hexane.

Sensor 140-7 was prepared with a ratio of 1:4. The sensor was tested in a closed 500-mL flask (its volume of gas was about 600 mL) with samples of hexane injected through the septum as described above. Again, a hollow needle through a septum served as a vent to air. The current was measured as a function of time with 0.2 V dc applied. The results are shown in FIG. 5. This Figure also shows the partial recovery after removing the sensor from the flask and exposing it to laboratory air. It was then placed back in the flask, which now contained 10 mL of hexane to saturate the air with hexane vapors, and FIG. 4 describes the response of the sensor.

Figure 6:
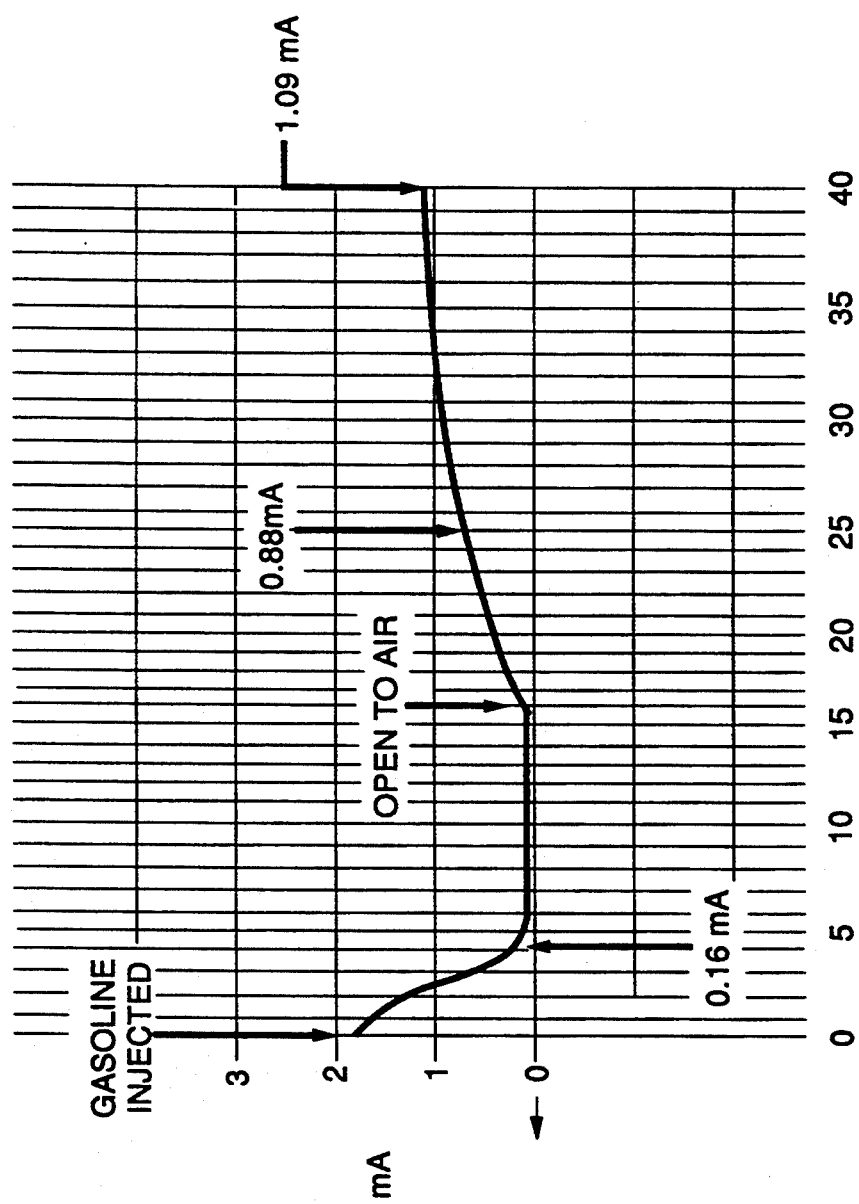
FIG. 6, on coordinates of sensor current (in mA) and time (in minutes), is a plot of current as a function of time employing yet another embodiment of the device of the invention in response to a gasoline vapor.

Another sensor was prepared with a ratio of 1:4 and was called 140-8. This sensor was tested in a 100-mL flask as described above for sensor 140-5, except that 100 μL of a standard gasoline, Unocal RF-A, was injected. The response of the sensor is shown in FIG. 6, which describes the drop in current from 1.74 mA to 0.16 mA during the exposure to gasoline vapors and part of the subsequent recovery upon removal to laboratory air.

Thus, there has been disclosed a sensor for detecting the presence of fugitive vapors. It will be readily apparent to those skilled in this art that various changes and modifications of an obvious nature may be made, and all such changes and modifications are considered to fall within the scope of the invention as defined by the appended claims.

What is claimed is:

1. A fugitive emissions sensor for reversibly detecting solvent vapors comprising:
   (a) a dielectric substrate having a major surface;
   (b) a pair of electrically conductive electrodes disposed on said major surface of said substrate, said electrodes each comprising a plurality of fingers interdigitated with the other electrode; and
   (c) a composite coating covering the interdigitated electrodes and comprising (1) a conductive polymer, said polymer having a conductivity in the range of $10^{-6}$ to 1 S/cm, and (2) a dielectric polymer with an affinity for said solvent vapors to be detected, the ratio of said conductive polymer to said dielectric polymer ranging from about 1:1 to 1:5.

2. The fugitive emissions sensor of claim 1 wherein said solvent vapors are selected from the group consisting of hydrocarbons and polar solvents.

3. The fugitive emissions sensor of claim 1 wherein said dielectric substrate comprises a material selected from the group consisting of glass, ceramics, and dielectric polymers.

4. The fugitive emissions sensor of claim 3 wherein said dielectric substrate comprises a glass selected from the group consisting of silica, phosphate, and borate glasses and mixtures thereof.

5. The fugitive emissions sensor of claim 3 wherein said dielectric substrate comprises a ceramic selected from the group consisting of alumina, magnesia, calcia and mixtures thereof.

6. The fugitive emissions sensor of claim 3 wherein said dielectric substrate comprises a dielectric polymer selected from the group consisting of polyethylene terephthalate, poly(tetrafluoroethylene), polymethyl methacrylate, and polyimides.

7. The fugitive emissions sensor of claim 1 wherein said electrically conducting electrodes comprise a material selected from the group consisting of gold, platinum, palladium, and carbon.

8. The fugitive emissions sensor of claim 7 wherein said electrically conducting electrodes both consist essentially of gold.

9. The fugitive emissions sensor of claim 8 wherein said gold electrodes are formed on an adhering layer that adheres said gold electrodes to said substrate.

10. The fugitive emissions sensor of claim 1 wherein said conductive polymer is selected from the group consisting of polyaniline, polythiophene, polypyrrole, poly(p-phenylene vinylene), derivatives of these polymers, and mixtures of these materials, with appropriate dopants present in an amount necessary to change said conductive polymer from a neutral state to a charged state to provide the requisite conductivity.

11. The fugitive emissions sensor of claim 10 wherein said conductive polymer is polyaniline and said dopants are selected from the group consisting of salts of p-toluenesulfonic acid, benzenesulfonic acid, p-dodecylsulfonic acid, poly(styrenesulfonic acid), sulfuric acid, and hydrochloric acid.

12. The fugitive emissions sensor of claim 1 wherein said solvent vapors comprise hydrocarbon solvents and said dielectric polymers are selected from the group consisting of poly(isobutylene), polybutadiene, polystyrene, and alkyl-substituted polystyrenes.

13. The fugitive emissions sensor of claim 1 wherein said solvent vapors comprise polar solvents and said dielectric polymers contain polar functional groups selected from the group consisting of hydroxyl, amino, and carboxylate groups.

14. A fugitive emissions sensor for reversibly detecting solvent vapors selected from the group consisting of hydrocarbons and polar solvents, comprising:
(a) a dielectric substrate having a major surface;
(b) a pair of electrically conductive electrodes disposed on said major surface of said substrate, said electrodes each comprising a plurality of fingers interdigitated with the other electrode; and
(c) a composite coating covering the interdigitated electrodes and comprising (1) a conductive polymer selected from the group consisting of polyaniline, polythiophene, polypyrrole, poly(p-phenylene vinylene), derivatives of these polymers, and mixtures of these materials, doped with appropriate dopants to provide a conductivity in the range of about $10^{-6}$ to 1 S/cm, and (2) a dielectric polymer with an affinity for said solvent vapors to be detected, said dielectric polymer selected from the group consisting of poly(isobutylene), polybutadiene, polystyrene, and alkyl-substituted polystyrenes where said solvent vapors to be detected comprise hydrocarbon solvents or said dielectric polymer containing polar functional groups selected from the group consisting of hydroxyl, amino, and carboxylate groups where said solvent vapors to be detected comprise polar solvents, the ratio of said conducting polymer to said dielectric polymer ranging from about 1:1 to 1:5.

15. A fugitive emissions sensor for reversibly detecting hydrocarbon solvent vapors comprising:
(a) a dielectric substrate having a major surface;
(b) a pair of electrically conductive electrodes disposed on said major surface of said substrate, said electrodes each comprising a plurality of fingers interdigitated with the other electrode; and
(c) a composite coating covering the interdigitated electrodes and comprising (1) a conductive polymer consisting essentially of polyaniline doped with p-toluenesulfonic acid to provide a sulfonate salt having a conductivity within the range of about $10^{-6}$ to 1 S/cm, and (2) a dielectric polymer consisting essentially of poly(iso-butylene), the ratio of said conducting polymer to said dielectric polymer ranging from about 1:1 to 1:5.

* * * * *